United States Patent
Pandian et al.

(10) Patent No.: US 6,627,457 B2
(45) Date of Patent: Sep. 30, 2003

(54) METHODS FOR DETECTING PREGNANCY

(75) Inventors: Murugan R. Pandian, Mission Viejo, CA (US); Julie Y. Lu, Mission Viejo, CA (US)

(73) Assignee: Quest Diagnostics Investments Incorporated, Wilmington, DE (US)

(*) Notice: Subject to any disclaimer, the term of this patent is extended or adjusted under 35 U.S.C. 154(b) by 208 days.

(21) Appl. No.: 09/918,297

(22) Filed: Jul. 30, 2001

(65) Prior Publication Data

US 2003/0022381 A1 Jan. 30, 2003

(51) Int. Cl.⁷ .................. G01N 33/53; G01N 33/536; G01N 33/48
(52) U.S. Cl. .................. 436/501; 436/65; 436/804; 436/818; 436/824; 436/510; 436/542; 436/536; 435/7.1; 435/7.8; 530/387.5; 530/388.24; 530/389.2
(58) Field of Search .................. 436/65, 804, 818, 436/824, 501, 510, 536, 542; 435/7.1, 7.8; 530/387.5, 388.24, 389.2

(56) References Cited

U.S. PATENT DOCUMENTS

| | | |
|---|---|---|
| 4,946,958 A | 8/1990 | Campbell et al. ........... 546/104 |
| 5,356,817 A | 10/1994 | Cole ........................ 436/64 |
| 5,506,150 A | 4/1996 | Canick et al. | 
| 5,660,990 A | 8/1997 | Rao et al. ................... 435/6 |
| 6,127,186 A | 10/2000 | Pandian |
| 6,339,143 B1 | 1/2002 | Krichevsky et al. ... 530/388.24 |
| 6,352,862 B1 | 3/2002 | Davis et al. ............... 436/510 |
| 6,429,018 B1 | 8/2002 | Cole et al. ................. 436/87 |
| 6,500,627 B1 | 12/2002 | O'Connor et al. .......... 435/7.92 |

FOREIGN PATENT DOCUMENTS

| | | |
|---|---|---|
| WO | 98/10282 | 3/1998 |
| WO | 99/41584 | 8/1999 |
| WO | 99/56132 | 11/1999 |
| WO | 00/42428 | 7/2000 |
| WO | 00/70094 | 11/2000 |

OTHER PUBLICATIONS

"Utility of Commonly Used Commercial Human Chorionic Gonadotropin Immunoassays in the Diagnosis and Management of Trophoblastic Diseases" by Cole et al; Clinical Chemistry, Feb. 2001, vol. 47, No. 2, pp. 305–315.

Bahado–Singh R et al., "A High–sensitivity alternative to 'routine' genetic amniocentesis: multiple urinary analytes, nuchal thickness, and age." Am J Obstet Gynecol Jan. 1999;180(1 Pt 1): 169–73.

Cole LA et al., "Urinary screening tests for fetal Down syndrome: I. Fresh β–core fragment." Prenat Diagn. Apr. 1999, 19(4): 340–50.

(List continued on next page.)

Primary Examiner—Jill Warden
Assistant Examiner—Monique T. Cole
(74) Attorney, Agent, or Firm—Stout, Uxa, Buyan & Mullins, LLP; Donald E. Stout; Greg S. Hollrigel

(57) ABSTRACT

Methods for detecting pregnancy in a woman comprise screening a biological sample of the woman for pregnancy markers. The methods of the invention include chemiluminescent assays for the pregnancy markers. The methods of the invention also comprise utilizing at least two capture antibodies that specifically bind different epitopes of the pregnancy marker in one assay. The methods of the invention permit detection of pregnancy within about 7 days after ovulation or implantation.

37 Claims, 1 Drawing Sheet

OTHER PUBLICATIONS

Bahado–Singh RO et al., "New triple screen test for Down syndrome: combined urine analytes and serum AFP." J Matern Fetal Med. 1998 May–Jun;7(3):111–4.

Kellner LH et al., "Levels of urinary beta–core fragment, total oestriol, and the ratio of the two in second–trimester screening for Down syndrome." Prenat Diagn. Dec. 1997;17(2):1135–41.

Cole La et al., "Combining beta–core fragment and total oestriol measurements to test for Down syndrome . . ." Prenat Diagn. Dec. 1997;17(12):1125–33.

Cuckle HS et al., "Urinary multiple marker screening for Down's syndrome." Prenat Diagn. Aug. 1995:15(8):745–51.

Bahado–Singh RO et al., "Comparison of urinary hyperglycosylated human chorionic gonadotropin concentration with the serum triple screen for Down syndrome detection in high–risk pregnacies." Am J Obstet Gynecol. Nov. 2000;183(5):1114–8.

Cole LA et al., "Urinary screening tests for fetal Down syndrome: II. Hyperglycosylated hCG." Premat Diagn. Apr. 1999;19(4):351–9.

Cole LA et al., "Hyperglycosylated hCG, a potential alternative to hCG in Down syndrome screening." Prenat Diagn. Sep. 1998; 18(9):926–33.

Hsu JJ et al., "Urine free beta–hCG and total estriol for Down syndrome screening during the second trimester in an Asian population." Obstet Gyncecol Jul. 1999;94(1):107–11.

Spencer K et al., "First–trimestar urine free beta hCG, beta core, and total oestriol in pregnancies affected by Down'syndrome: implications for first–trimester screening with nuchal translucency and serum free beta hCG." Prenat Diagn Jun. 1997;17(6):525–38.

Isozaki T et al., "Screening for Down syndrome pregnancy using β–core fragment: prospective study." Prenat Diagn May 1997;17(5):407–13.

Spencer K et al., "Urine free beta hCG and beta core in pregnancies affected by Down's syndrome." Prenat Diagn Jul. 1996;16(7):605–13.

Krichevsky A et al., "The development of panel of monoclonal antibodies to human luteinizing hormone and its application to immunological mapping and two–site assays." Endocrine 1994, 2, 551–520.

O'Conner JF et al, Differential Urinary Gonadotrophin Profiles in Early Pregnancy and Early Pregnancy Loss. Prenat Diagn 18: 1232–1240 (1998).

Unknown "Serum Hyperglycosylated hCG: a Potential Screening Test for Fetal Down Syndrome." Prenat. Diagn. 19:488–490 (1999).

Cole LA et al., "Hyperglycosylated Human Chorionic Gonadotropin (Invasive Trophoblast Antigen) Immunoassay: A New Basis for Gestational Down Syndrome Screening." Clinical Chemistry 45:12 2109–2119. 1999).

Abushoufa RA et al, "The development of a sialic acid specific lectin–immunoassay for the measurement of human chorionic gonadotrophin glycoforms in serum and its application in normal and Down's syndrome pregnancies." Clinical Endocrinology (2000) 52, 499–508.

Birken S. et al., "Development and Characterization of Antibodies to a Nicked and Hyperglycosylated Form of hCG from a Choriocarcinoma Patient." Endocrine, 10:(2) 137–144 Apr. 1999.

Krichevsky A. et al., "Development, Characterization, and Application of Monoclonal Antibodies to the Native and Synthetic βCOOH–Terminal Portion of Human Chorionic Gonadotropin (hCG) That Distiguishes between the Native and Desialylated Forms of hCG" Endocrinology Mar. 1994;134(3):1139–45.

Krichevsky A. et al. "Development and Characterization of a New, Highly Specific Antibody to the Human Chorionic Gonodotropin–β Fragment." Endocrinology Mar. 1991;128(3):1255–64.

METHODS FOR DETECTING PREGNANCY

SUMMARY OF THE INVENTION

The present invention provides methods for detecting pregnancy in a woman. In particular, the methods comprise screening biological samples for biological markers associated with pregnancy. One aspect of the invention is related to the discovery that using a combination of two capture antibodies that specifically bind different epitopes of ITA in one assay improves the sensitivity of the assay for the biological markers.

In one embodiment of the invention, a method for detecting pregnancy in a woman comprises the step of: contacting a biological sample of the woman with antibodies that bind invasive trophoblast antigen (ITA), in a chemiluminescent assay, wherein the assay comprises at least two antibodies that specifically bind different epitopes of the ITA, wherein a label coupled to at least one of the two antibodies produces a detectable signal, and wherein the presence of a detectable signal indicates pregnancy in the woman.

In another embodiment of the invention, a method for detecting pregnancy in a woman comprises contacting a biological sample of the woman with antibodies that bind ITA in an assay, wherein the assay comprises at least two antibodies that specifically bind different epitopes of ITA, wherein a label coupled to at least one of the two antibodies produces a detectable signal.

In another embodiment of the invention, a method for detecting pregnancy in a woman comprises contacting a biological sample of the woman with antibodies that bind at least one pregnancy marker in one assay, wherein the assay comprises at least two capture antibodies that specifically bind different epitopes of the marker, and at least one detection antibody that specifically binds an epitope of the marker different from the epitopes bound by the capture antibodies, and wherein a label coupled to the detection antibody produces a detectable signal. In certain embodiments, the pregnancy markers comprise ITA, human chorionic gonadotropin (hCG), or fragments thereof. In other embodiments of the invention, the pregnancy markers comprise a combination of ITA and hCG, or fragments thereof.

In another embodiment of the invention, a method for detecting pregnancy in a woman comprises contacting a biological sample of the woman with antibodies that bind ITA in one assay, wherein the assay comprises at least two capture antibodies that specifically bind different epitopes of ITA, and at least one detection antibody that binds an epitope of ITA different from the epitopes bound by the capture antibodies, and wherein a label coupled to the detection antibody produces a detectable signal.

The foregoing methods can also be practiced by contacting the biological sample with antibodies that bind at least one additional pregnancy marker, such as hCG, or a fragment thereof.

In yet another embodiment of the invention, a method for detecting pregnancy in a woman comprises contacting a biological sample of the woman with antibodies that bind ITA and hCG, in one assay, wherein the assay comprises at least two capture antibodies that specifically bind different epitopes of the ITA and hCG, and at least one detection antibody that binds an epitope of the ITA and hCG different from the epitopes bound by the capture antibodies, and wherein a label coupled to the detection antibody produces a detectable signal.

In certain embodiments of the invention, the capture and detection antibodies of the foregoing methods are monoclonal antibodies. Examples of capture antibodies include monoclonal antibodies designated B152, clone 827, and clone 820. Examples of detection antibodies include the monoclonal antibody designated B207.

In another embodiment of the invention, a method for detecting pregnancy in a woman comprises a) contacting a biological sample of the woman with a capture antibody designated B152; and b) contacting the biological sample with a detection antibody designated B207, wherein the capture and detection antibodies recognize and bind different epitopes of ITA, and wherein the the detection antibody is coupled to a label that produces a detectable chemiluminescent signal.

In yet another embodiment of the invention, a method for detecting pregnancy in a woman comprises contacting a biological sample of the woman with antibodies that bind ITA and hCG, in one assay, wherein the assay comprises at least two capture antibodies, designated B152 and clone 827, that specifically bind different epitopes of the ITA and hCG, and at least one detection antibody, designated B207, that binds an epitope of the ITA and hCG different from the epitopes bound by the capture antibodies, and wherein the detection antibody is coupled to a label that produces a detectable signal.

The biological samples used in the methods of the invention include liquid or tissue samples. Liquid samples include urine, whole blood, serum, plasma, or amniotic fluid. Tissue samples include vaginal tissue or placental tissue.

In some embodiments of the invention, the detectable signals may be obtained by measuring the luminescence of an acridinium ester.

The foregoing methods can be practiced within about seven days after ovulation or in vitro fertilization. In some embodiments, the methods are practiced within about five days of ovulation, or within about four days of in vitro fertilization.

The assays of the foregoing methods may be automated.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DETAILED DESCRIPTION OF THE INVENTION

Figure 1A:
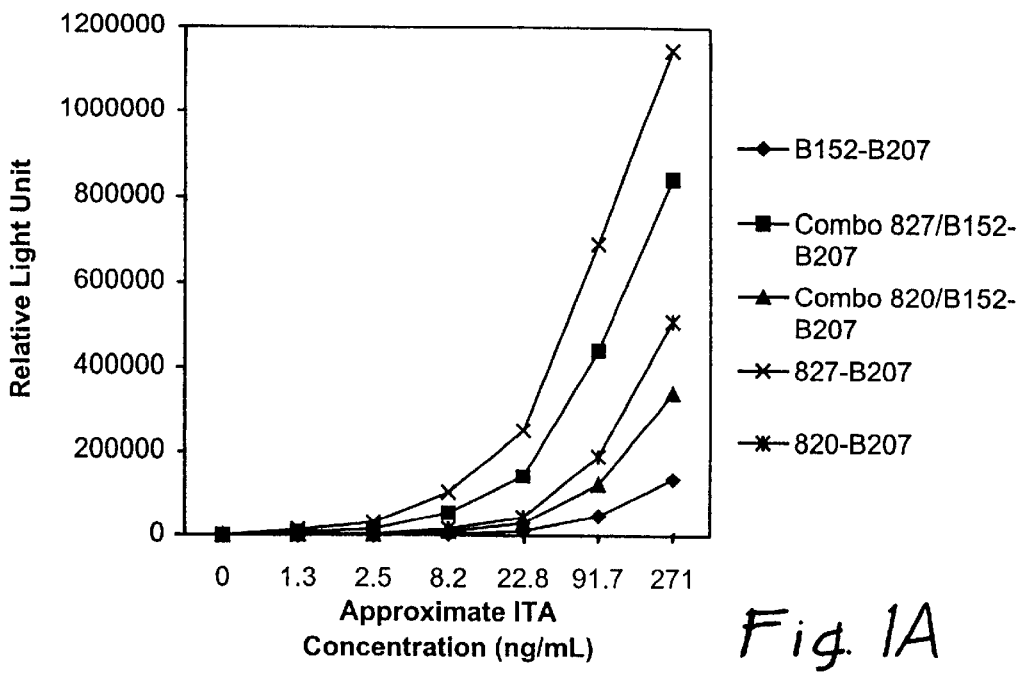
FIG. 1 depicts graphs of relative light unit versus approximate ITA concentration (ng/mL).
FIG. 1B is a magnified version of FIG. 1A depicting the data at ITA concentrations of approximately 0 ng/mL and approximately 1.3 ng/mL. The data are from five assays as described in Examples 1–3, infra. The symbols represent assays of specific capture antibody-detection antibody combinations. The closed diamonds (♦) represent the B152-B207 assay. The closed squares (■) represent the combination assay of clone 827/B152-B207. In particular, the monoclonal antibodies, clone 827 and B152, were the capture antibodies; and the monoclonal antibody B207 was the detection antibody. The closed triangles (▲) represent the combination assay of clone 820/B152-B207. The 'x' (x) represent the clone 827. B207 assay. In particular, the monoclonal antibody, clone 827, was the capture antibody and the monoclonal antibody B207 was the detection antibody. The asterisks (*) represent the clone 820-B207 assay.

Unless defined otherwise, all technical and scientific terms used herein have the same meaning as commonly understood by those of ordinary skill in the art to which this invention belongs. For purposes of the present invention, the following terms are defined below.

As used herein, "invasive trophoblast antigen" (ITA) is a glycoprotein hormone secreted by trophoblast cells of the placenta of pregnant women. ITA is also called hyperglycosylated hCG. ITA is similar, to C5 hCG, which is a nicked h-hCG obtained from a choriocarcinoma patient. ITA, as defined, also includes fragments of ITA, or variants of ITA. In particular, ITA encompasses molecules that exhibit similar biological activities or expression patterns to ITA and that exhibit aberrant carbohydrate levels as compared to normally glycosylated hCG including, nicked hCG, α-subunits of hCG, β-subunits of hCG, or any combination thereof. Examples of ITA isoforms include isoforms that comprise 57% triantennary N-linked oligosaccharides and 68% hexasaccharide-type O-linked oligosaccharides. Another ITA isoform may comprise 48% triantennary N-linked oligosaccharides and 100% hexasaccharide-type O-linked oligosaccharides. In normal pregnancies, a relatively small proportion of more complex triantennary N-linked oligosaccharides (0–30%) and larger hexasaccharide-type O-linked sugar units (0–20%) are also found.

As used herein, a "pregnancy marker" is defined as a molecule that has an expression pattern or biological activity related to pregnancy. Pregnancy markers include ITA, hCG, and fragments thereof. Other examples of pregnancy markers include, but are not limited to, beta-subunit hCG, beta-core hCG, unconjugated estriol (UE3), alpha-fetoprotein (AFP), leptin, prorenin, renin, DHEA-S, leukocyte acid phosphatase, inhibin, pregnancy associated plasma protein A (PAPP-A), AFP-L3, P43, superoxide dismutase (SOD), proMBP, fetal DNA, insulin-like growth factor binding proteins 3 (IGFBP3), CA 125, placental lactogen, Hp2FF, serum sialytransferase, s100b protein, schwangers chafts protein 1 (SPI), activin A/follistatin, fetal antigen (FA-2), and placental alkaline phosphatase (PALP).

In one embodiment of the invention, ITA comprises fragments of ITA. For example, greater nicking is observed in ITA preparations compared to hCG preparations. For example, ITA may be nicked or cleaved at similar sites on its beta subunit, and dissociate to form a free alpha subunit and a nicked free hyperglycosylated beta-subunit. Nicked free beta-subunit of ITA can be further degraded to a beta-subunit core fragment comprising short disulfide-linked peptides, with traces of hyperglycosylation sugar moieties.

As used herein, "antibody" refers to a polypeptide substantially encoded by an immunoglobulin gene or immunoglobulin genes, or fragments thereof, which specifically recognize and bind an antigen. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. The term "antibody," as used herein, also includes antibody fragments either produced by the modification of whole antibodies or those synthesized de novo using recombinant DNA methodologies, and further includes "humanized" antibodies made by now conventional techniques.

An antibody "specifically binds to" or "is immunoreactive with" a protein when the antibody functions in a binding reaction with the protein. In order for the antibody to bind to a protein, the protein should contact the antibody. Accordingly, contacting a sample suspected of containing an antigen of interest with an antibody to the antigen will permit the antibody to specifically bind the antigen. The binding of the antibody to the protein permits determination of the presence of the protein in a sample in the presence of a heterogeneous population of proteins and other agents. Thus, under designated immunoassay conditions, the specified antibodies bind preferentially to a particular protein and do not significantly bind to other proteins present in the sample. Specific binding to a protein under such conditions requires an antibody that is selected for specificity for a particular protein. Several methods for determining whether or not a peptide is immunoreactive with an antibody are known in the art.

As used herein, a "capture antibody" is defined as an antibody, preferably a monoclonal antibody, attached to a substrate, such as a solid substrate. The capture antibody is selected to specifically bind a particular, distinct epitope of an antigen, such as ITA or hCG.

As disclosed herein, one capture antibody is designated B152, and may be attached to a solid substrate comprising magnetic particles. Monoclonal antibody B152 specifically binds ITA. The hybridoma producing the B152 monoclonal antibody was deposited on Feb. 3, 1998 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. The hybridoma was accorded ATCC Accession Number HB-12467. The B152 antibody was raised against C5 hCG, as disclosed in WO 98/10282, Prenatal Screening for Down's Syndrome Using Hyperglycosylated Gonadotropin; Cole et al., (1998) Hyperglycosylated hCG, a Potential Alternative to hCG in Down Syndrome Screening, Prenatal Diagnosis, 18:926–933; Cole et al., (1999) Hyperglycosylated Human Chorionic Gonadotropin (Invasive Trophoblast Antigen) Immunoassay: A New Basis for Gestational Down Syndrome Screening, 45:2109–2119. Hybridomas producing the B152 monoclonal antibody were obtained from Columbia University.

Another capture antibody used to practice the methods of the invention is the publicly available monoclonal antibody clone 820 available from Biodesign International, Saco, Me. (Catalog Number E45550M). Clone 820 is a monoclonal antibody to hCG. Clone 820 specifically binds to intact hCG (cross reactivity is 100%). The cross reactivity with beta-hCG is less than 1.0%, with alpha-hCG is less than 1.0%, with luteinizing hormone is less than 0.1%, with thyroid stimulating hormone is less than 0.1%, and with follicle stimulating hormone is less than 1.0%. However, as described in Example 2, infra, Clone 820 may also specifically bind ITA, because the ITA standards were reactive with the Clone 820. Clone 820 was produced in mouse, and is an IgG1 isotype. The hybridoma was prepared by fusing myeloma cells with spleen cells from Balb/c mice. Purified Clone 820 is stored in liquid format at a concentration of 5.64 mg/mL in 0.015 M potassium phosphate buffer, 0.15 M NaCl, at a pH of 7.2. The preservative is 0.1% sodium azide.

Another capture antibody used to practice the methods of the invention is the publicly available monoclonal antibody clone 827 available from Biodesign International, Saco, Me. (Catalog Number E45575M). Clone 827 is a monoclonal antibody to the beta subunit of hCG. Clone 827 specifically binds to beta-hCG (cross reactivity is 100%). The cross reactivity with intact hCG is 0.5%, with alpha-hCG is less than 0.1%, with luteinizing hormone is less than 0.1%, with thyroid stimulating hormone is less than 0.1%, and with follicle stimulating hormone is less than 0.1%. However, as described in Example 3, infra, Clone 827 may also specifically bind ITA, because the ITA standards were reactive with the Clone 827. Clone 827 was produced in mouse, and is an IgG1 isotype. The hybridoma was prepared by fusing myeloma cells with spleen cells from Balb/c mice. Purified Clone 827 is stored in liquid format at a concentration of 4.44 mg/mL in 0.015 M potassium phosphate buffer, 0.15 M NaCl, at a pH of 7.2. The preservative is 0.1% sodium azide.

As used herein, a "detection antibody" is defined as an antibody, preferably a monoclonal antibody, that binds an antigen at a binding site or epitope distinct from that of the capture antibody. As is understood in the art, depending on the amount of cross-reactivity that is desired for related antigens, the specificity of the detection antibody may vary. For example, and as discussed herein, for combination assays where two or more antigens are assayed, it may be desirable to use two capture antibodies that specifically bind each antigen, and one detection antibody that will bind an epitope similar or identical on both antigen molecules.

In certain embodiments of the invention, the detection antibody is a monoclonal antibody that recognizes the beta subunit of hCG or the beta subunit of ITA. One example is a monoclonal antibody designated B207. Monoclonal antibody B207 was generated to the beta subunit of hCG, but is cross reactive with the beta subunit of ITA. The hybridoma producing the B207 monoclonal antibody was deposited with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. The hybridoma was accorded ATCC Accession Number PTA 1626. The B207 mAb was developed and described in Krichevsky et al., (1994) The Development of a Panel of Monoclonal Antibodies to Human Luteinizing Hormone and its Application to Immunological Mapping and Two-Site Assays, Endocrine, 2:511–520; WO 99/41584, Methods for Predicting Pregnancy Outcome in a Subject by hCG Assay; and WO 00/70094, Methods for Predicting Pregnancy Outcome in a Subject by hCG Assay; O'Connor et al., (1998) Differential Urinary Gonadotrophin Profiles in Early Pregnancy and Early Pregnancy Loss, Prenatal Diagnosis, 18:1232–1240. The hybridoma for the B207 mAb was obtained from Columbia University.

The detection antibody is coupled to a label, as described herein. The concentration of detection antibody used in practicing the methods of the invention is predetermined and optimized by conducting experiments to determine amounts of detection antibodies that are needed to provide a detectable signal. It will be understood by persons skilled in the art that a sufficient concentration of detection antibody is provided to ensure binding of the detection antibody to all, or essentially all, of the test antigen molecules. In other words, it is preferable to use as much detection antibody as possible without increasing non-specific binding of the detection antibody in the assay to improve the signal-to-noise ratio of the device of the invention.

In certain embodiments of the invention, capture antibodies are monoclonal antibodies that specifically bind two different epitopes of an antigen. For example, the two capture antibodies may bind an epitope on the beta subunit of ITA, and an epitope on the alpha subunit of ITA. Alternatively, the two capture antibodies may bind an epitope on the alpha subunit and an epitope on the beta subunit of hCG. For ITA, examples of capture antibodies include monoclonal antibodies B152, clone 820, and clone 827, as described herein. For other antigens, other antibodies may be produced and screened using conventional immunological techniques. In addition, the detection antibodies may be monoclonal antibodies that bind the antigen at an epitope that does not interfere with the binding of the capture antibodies to the antigen. The detection antibodies can be relatively less specific than the capture antibodies. For example, the detection antibodies can cross react with another antigen that is antigenically similar to the first antigen. One example would be a detection antibody that binds an epitope on the beta subunit of hCG, and an epitope on the beta subunit of ITA. In one embodiment of the invention, the detection antibody is designated B207, as described herein.

A "label" is a composition detectable by spectroscopic, photochemical, biochemical, immunochemical, or chemical means. In other words, a label produces a detectable signal in practicing the methods of the invention. For example, useful labels include fluorescent dyes, chemiluminescent compounds, radioisotopes, electron-dense reagents, enzymes, colored particles, biotin, or dioxigenin. A label often generates a measurable signal, such as radioactivity, fluorescent light, color, or enzyme activity, which can be used to quantitate the amount of bound label.

Examples of chemiluminescent compounds include luciferin, a luminol derivative, pyrogallol, isoluminol, aequorin, cyclic arylhydrazides, dioxetanes, rhodium chelates (electrochemiluminescent), oxalate esters, thermochemiluminescent labels, acridinium and the like. These labels may be attached to a protein, for example an anti-ITA antibody, using techniques well known in the art. (See U.S. Pat. No. 5,284,952, the disclosure of which is incorporated in its entirety herein by reference.) In one embodiment, a detection antibody, such as B207, may be labeled with an acridinium ester by employing the methods found in U.S. Pat. Nos. 5,284,952, 5,110,932, and 5,338,847, the disclosures of which are incorporated in their entirety herein by reference.

Examples of the fluorescent material to be used for labeling include fluorescein, fluorescamine, fluorescein isothiocyanate, umbelliferone, rhodamine, Texas red dyes, pthalocyanines, coumarin, squaraine, anthracene, erythrosine, europium chelates and the like.

Examples of radioactive isotopes to be used for labeling include $^{14}C$, $^{3}H$, $^{32}P$, $^{18}F$ or $^{125}I$.

Exemplary enzymes which have been developed and can be used in assays of the invention are those described in U.S. Pat. Nos. 3,654,090; 3,791,932; 3,839,153; 3,850,752; 3,817,837; 3,879,262; Journal of Immunological Methods 1: 247(1972); and the Journal of Immunology 109:129(1972), the disclosures of which are incorporated in their entirety herein by reference. Other examples of enzymes include, but are not limited to, alkaline phosphatase, beta galactosidase, horseradish peroxidase, gluconidase, phosphatase, peptidase, alkaline phosphatase and the like. Co-enzymes useful in this invention include molecules and/or proteins which facilitate an enzyme to catalyze a reactant to produce a detectable product, for example light. A co-enzyme may include, without limitation, FAD and NAD.

Examples of colored particles include colloidal gold, or blue latex.

Other labels may include a non-active precursor of a spectrophotometrically-active substance (British Pat. No.

1,392,403 and French Pat. No. 2,201,299, which patents correspond to U.S. Pat. No. 3,880,934) and electron spin resonance moieties (U.S. Pat. No. 3,850,578).

As described herein, certain parameters of the assays used to practice the methods of the invention are determined prior to practicing the methods. For example, the components of the solutions and their concentrations (e.g., the concentrations of capture and detection antibodies); the experimental conditions of the assays, such as buffer solution, pH, ionic strength, temperature, incubation times, solid phase support; the coupling chemistry between the support and the various antibodies, and the coupling chemistry between the detection antibody and the label, are preferably predetermined by conducting conventional experiments to optimize the methods of the invention.

The present invention is, in part, based upon the discovery that pregnancy may be detected with increased sensitivity and accuracy by measuring a woman's level of ITA with a combination of antibodies, as disclosed herein. The methods disclosed herein may also be useful in determining whether a pregnant woman is pregnant with a fetus that has Down's syndrome.

The methods for detecting pregnancy disclosed herein comprise contacting a biological sample of a woman with antibodies that bind to ITA, alone or in combination with other antigens or biological markers (pregnancy markers), and comparing the amount of measured antigens (e.g., ITA) to a standard that has been determined to reflect the likelihood of a woman being pregnant.

Elevated urine or serum hCG levels are a common marker of pregnancy, with suitable threshold values for pregnancy being in the range from about 25 mIU/mL to about 100 mIU/mL (IU means International Units; 25 mIU/mL corresponds to approximately 1.79 ng/mL of hCG). Thus, the hCG concentration is typically an indication that the woman being tested is pregnant. It is believed that ITA levels increase before the increase in hCG levels. Thus, measuring the concentration of ITA in a biological sample provides a marker to detect pregnancy before hCG levels increase.

Biological samples useful for practicing the methods of the invention include, but are not limited to, whole blood, serum, urine, plasma, and amniotic fluid. In addition, the samples may include tissue samples, such as, for example, tissue from the placenta, vagina, or uterus of a pregnant woman. In one embodiment of the invention, the biological sample is urine.

Samples may be obtained from pregnant women by any conventional method known to those skilled in the art. For example, serum samples may be obtained by withdrawing a volume of blood from the pregnant woman using conventional intravenous techniques. Amniotic samples can be obtained by withdrawing amniotic fluid from pregnant women using a needle and syringe. Urine samples can be obtained from the pregnant woman.

Screening the biological sample for ITA may be performed by contacting the sample with antibodies that specifically bind ITA.

In one embodiment of the invention, "sandwich" type immunoassays are utilized to measure ITA in a sample. The methods of the invention may utilize a capture antibody that specifically binds to the ITA. The capture antibody may be coupled to a solid substrate or solid phase. Examples of suitable substrates include, but are not limited to, wells of microtiter plates or cuvettes, or nitrocellulose or nylon membranes. In one embodiment of the invention, the capture antibodies are coupled to paramagnetic particles in wells of microtiter plates or cuvettes. For example, biotin-coupled capture antibodies can couple to streptavidin coated paramagnetic particles via the well known avidin-biotin binding reaction. Other methods of coupling the capture antibody to the solid phase of the assays are known to those skilled in the art. In one embodiment of the invention, the capture antibody is designated B152. The B152 monoclonal antibody specifically binds ITA as described in WO 98/10282, Prenatal Screening for Down's Syndrome Using Hyperglycosylated Gonadotropin; WO 99/41584, Methods for Predicting Pregnancy Outcome in a Subject by hCG Assay; WO 00/70094, Methods for Predicting Pregnancy Outcome in a Subject by hCG Assay; O'Connor et al., (1998) Differential Urinary Gonadotrophin Profiles in Early Pregnancy and Early Pregnancy Loss, Prenatal Diagnosis, 18:1232–1240; Cole et al., (1999) Hyperglycosylated Human Chorionic Gonadotropin (Invasive Trophoblast Antigen) Immunoassay: A New Basis for Gestational Down Syndrome Screening, Clinical Chemistry, 45:2109–2119; Cole et al., (1999) Urinary Screening Tests for Fetal Down Syndrome: II. Hyperglycosylated hCG, Prenatal Diagnosis, 19:351–359; and Shahabi et al., (1999) Serum Hyperglycosylated hCG: a Potential Screening Test for Fetal Down Syndrome, Prenatal Diagnosis, 19:488–490.

In practicing the sandwich immunoassay, ITA may also be exposed to a detection antibody that is coupled to a detectable label. Examples of suitable labels are described above, one example of a label is an acridinium ester. Methods of coupling labels to antibodies are well known in the art. For example, acridinium, as a "sulfonyl chloride ester" can be crosslinked to the detection antibody by the reaction of the lysly moiety of the epsilon amino group of lysine in proteins, such as antibodies, to the acridinium ester. The reaction products may then be separated by size exclusion chromatography on Sepharose beads. One detection antibody is designated B207. B207 was developed to the hCG β fragment as described in Krichevsky et al., (1994) The Development of a Panel of Monoclonal Antibodies to Human Luteinizing Hormone and its Application to Immunological Mapping and Two-Site Assays, Endocrine, 2:511–520.

In certain embodiments of the invention, the sandwich immunoassays are chemiluminescent immunoassays. The range of sensitivity of ITA concentration of the assays disclosed herein is from about 1 to about 300 ng/mL, but sensitivities of about 0.1 ng/mL are also encompassed. Cross-reactivity of the antibodies used in the methods of the invention with hCG, β-hCG, and nicked hCG may be less than about 4.5%.

Although specific monoclonal antibodies are disclosed herein, other monoclonal antibodies that could be used as capture and detection antibodies for ITA as described herein can be produced using conventional methods known in the art. See, for example, Kohler and Milstein,(1975) Nature, 256:495–97; or Sambrook et al. (2001) Molecular Cloning: A Laboratory Manual, 3rd edition, Cold Spring Harbor Laboratory Press. Briefly, animals, such as mice, are injected with an antigen, such as ITA, or fragments thereof, that may be coupled to a carrier protein. The animals are boosted with one or more antigen injections, and are hyperimmunized by an intravenous (IV) booster about three days before fusion. Spleen cells from the mice are isolated and are fused by standard methods to myeloma cells. Hybridomas are selected in standard hypoxanthine/aminopterin/thymine (HAT) medium, according to standard methods. Hybridomas secreting antibodies which recognize different epitopes of the antigen are identified, cultured, and subcloned using standard immunological techniques. The antibodies are then screened for the desired specificity or cross reactivity using methods known in the art.

Although one embodiment of the invention employs chemiluminescent sandwich immunoassays to practice the methods of the invention, other immunoassays, such as ELISAs and RIAs may be used. The parameters and components of the assays are determined and optimized as is well known to those skilled in the art such that the assays provide measurement of ITA levels in the biological samples being assayed. In addition, although certain embodiments of the invention utilize antibodies as the agents capturing the ITA, ITA may be captured in the assays of the invention using other chemical agents or molecules that are not antibodies. For example, such an agent may recognize carbohydrate profiles of ITA, and thereby bind the ITA to a solid phase in a similar manner as the capture antibodies described herein.

In some embodiments of the invention, it may be desirable to automate the methods as much as practical in order to improve replicability of the results and reduce the time and costs required to conduct the assays. Automated assays used to practice the methods of the invention permit users to conduct at least about 80 tests per hour, and preferably more than about 100 test per hour.

One may also use any conventional, non-automated, assay device to practice the methods of the invention. For example, a conventional microtiter plate can be used to store the various solutions used in performing the assay. The device should permit the biological sample to be exposed to a combination of antibodies. The antibodies may recognize different epitopes of the antigen(s) being assayed. The device should also cause the bound antigen to be retained to a substrate as solutions are added and removed during the assay.

By way of example, and not by way of limitation, wells of a microtiter plate can be loaded with a solution containing streptavidin coated magnetic particles, as described herein. A solution containing biotin coupled capture antibodies (e.g., biotin coupled B152 mAb) is added to the well to enable the coupling of the capture antibodies to the magnetic particles. A concentration of capture antibody is empirically selected (based on expected antigen concentrations) as discussed herein, to permit binding of all, or essentially all, of the test antigen that is available in the sample. In that regard, typical antigen concentrations in biological samples are in the nanogram to low microgram range (e.g. 1 ng/ml-5 $\mu$g/ml) so that the capture antibody concentrations are in the low to high microgram range (e.g. 1–100 $\mu$g/ml). The sample is added to the well. If the sample contains the antigen of interest (e.g., ITA), the antigen will bind to the capture antibodies. The plate is exposed to a magnetic field to immobilize the magnetic particles, and the solution is removed from the well; but the antigen will not be removed because it is bound to the antibodies that are bound to the magnetic particles that are immobilized by the magnetic field. A solution containing the detection antibody coupled to a label (e.g., acridinium labeled B207 mAb) is added to the well containing the bound antigen. As indicated elsewhere herein, the concentration of the detection antibody is preferably selected so that all, or essentially all, of the test antigen molecules (e.g., ITA) are bound by the detection antibody. Thus, the detection antibody can be provided at concentrations at least an order of magnitude greater than the expected concentration of the test antigen. For example, if a test antigen has an expected concentration of 100 ng/ml, the detection antibody concentration can be 1000 ng/ml (1 $\mu$g/ml). After a sufficient amount of time (from about 10 minutes to about 8 or more hours), determined and optimized empirically as described herein, the plate is exposed to a magnetic field, the solution is then removed, and the sample is washed. The amount of label remaining in the well is then measured (e.g., by a luminometer). The measured values can be quantitative or qualitative. Quantitative results are usually preferred. The measured values may then be compared to a standard or a threshold.

The Nichols Advantage® immunoassay system is a fully automated chemiluminescent system that may be used to practice the methods of the invention. The system is a bench-top instrument that performs solid phase chemiluminescent immunoassays. Steptavidin-coated magnetic particles and biotinylated antibodies may be employed in the assay system. Acridinium ester is typically the chemiluminescence label for signal detection. The Advantage immunoassay system has the flexibility to use different formats, optimizing incubation time for each individual assay. The system supports three different assay formats:

1) a simultaneous assay format in which antibodies and solid phase are incubated with the samples at the same time;
2) a sequential assay format in which antibodies are incubated with the samples, streptavidin-coated magnetic particles are added, followed by a farther incubation step; and
3) a two step assay format that involves binding of one antibody and the solid phase to the antigen followed by a wash step, and the addition of labeled antibody followed by a second incubation. Other features of the system include on board refrigeration, primary tube sampling, automatic clot and bubble detection, and ready to use reagent cartridges.

In practicing the methods of the invention, a control may be provided in the assay to ensure that the reactions have been successful. For example, a control could be provided with a polyclonal antibody solution for other analytes present in the biological sample. A specific example could be to detect the presence of progesterone, or metabolites thereof, in the sample. If the methods are practiced and the test results for the sample and the control are negative, or if the sample is positive and the control is negative (e.g., there is no detectable signal), it is likely to mean that the woman was either not pregnant to begin with, that an error has been made in the testing protocol, or that the test materials have been compromised in some manner. Alternatively, if a signal is detected in the sample reaction zone and in the control, it is likely that the woman is pregnant.

The following examples are presented to illustrate assays and methods used for detecting pregnancy. The methodology and results may vary depending on the parameters of the assays being used, as well as the antigens being screened. The examples are not intended in any way to otherwise limit the scope of the invention.

EXAMPLES

Example 1

ITA Chemiluminescent Assay

The methods set forth below were performed on a Nichols Advantage® assay system (Nichols Institute Diagnostics (NID), San Juan Capistrano, Calif.).

A series of solutions are provided and stored in individual vials or containers, as described herein. An assay buffer solution comprises 4% protease-free bovine serum albumin (BSA) in 0.5 M phosphate buffer saline (PBS; pH 7.6). A capture antibody solution comprises 4.2 $\mu$g/mL (or 0.42 $\mu$g/test) of biotin-coupled capture antibody (B152), 0.5% protease free BSA in 0.5 M PBS, 6% normal mouse serum, and 0.1% mouse gamma globulin at a pH of 7.4. A magnetic particle solution comprises 4 mg/mL of steptavidin coated magnetic particles (M270; Dynal Biotech, Inc., Lake Success, N.Y.) in normal mouse serum. A detection antibody solution comprises about 0.1 μg/test of an acridinium ester-labeled detection antibody (B207), 0.4% BSA in 0.1 M PBS at a pH of 6.0. A wash solution comprises a detergent, such as Tween®, in PBS with 0.1% sodium azide as a preservative.

The assay was performed by adding 15 μL of a sample or a standard (such as an ITA standard), 260 μL of the assay buffer, 70 μL of the capture antibody solution, and 25 μL of the magnetic particle solution to a well in a plate or cuvette. The solution was allowed to incubate for 30 minutes at 37 degrees C.

After incubation, the plate was exposed to a magnetic field to immobilize the ITA/capture antibody/magnetic particle complex. The supernatant was removed and the well was washed with the wash solution. After sufficient washing, determined and optimized empirically, the plate was removed from the magnetic field, and 50 μL of the detection antibody solution and 250 μL of the normal mouse serum was added to the well. The solution incubated for about 10 minutes at 37 degrees C. Subsequently, the plate was again exposed to a magnetic field to immobilize the detection antibody/ITA/capture antibody/magnetic particle complex. The supernatant was removed and the well was washed. An acid solution comprising hydrogen peroxide in a diluted acid, such as HCl, and a base solution comprising diluted sodium hydroxide were then added to the well to trigger the signal of the acridinium ester. The amount of detected signal was then measured in a luminometer, and the data were recorded. If the detected signal exceeded the sensitivity range of the assay, the sample was diluted with a diluent comprising 0.1% protease free BSA in 0.5 M PBS at pH of 7.4.

Figure 1B:
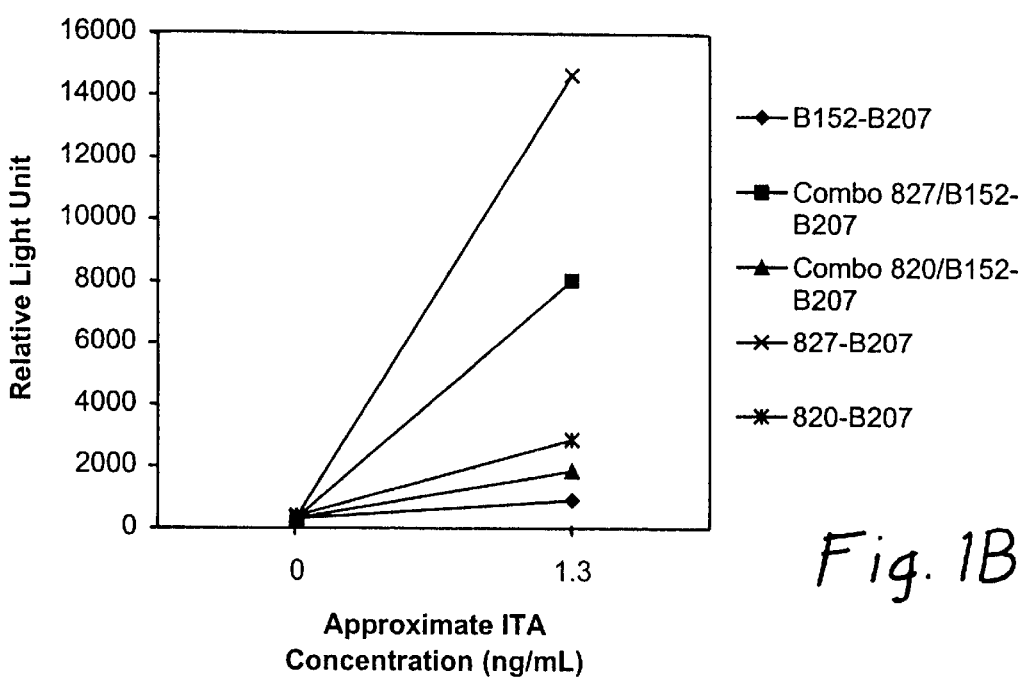

The assay was calibrated using six ITA standards. The ITA standards had ITA concentrations of about 1.3 ng/mL; about 2.5 ng/mL; about 8.2 ng/ml; about 22.8 ng/mL; about 91.7 ng/mL; and about 271 ng/mL. The calculated relative light units (RLU) for each standard were 914 RLU; 1,630 RLU; 4,873 RLU; 12,794 RLU; 48,149 RLU; 135,384 RLU, respectively. The baseline RLU (i.e., when the ITA concentration was 0 ng/mL) was 314 RLU. The results of this assay are depicted in FIGS. 1A and 1B designated by the closed diamond (♦).

A urine sample of a woman was screened for ITA, as described above. The urine sample had a detectable signal of 1,095 RLU. Based on the ITA standard data, this correlated to an ITA concentration of 1.6 ng/mL.

Example 2

ITA/Intact hCG Assay

A combination assay ("combo" assay) was also performed using the B152-B207 assay described in Example 1; however, an additional capture antibody that specifically binds intact hCG was added to the well during the first incubation with the B152 capture antibody and the ITA. The antibody used was designated clone 820 (purchased from Biodesign International, Saco, Me.; Cat. No. E45550M). This assay is referred to herein as the "combo 820/B152-B207" assay. In particular, in this combo assay, the capture antibodies are the clone 820 and the B152 monoclonal antibodies, and the detection antibody is the B207 monoclonal antibody. The results of this assay are illustrated in FIGS. 1A and 1B designated by the closed triangle (▲).

Unexpectedly, the detected signal of ITA appeared to be substantially greater than the detected signal using the B152-B207 assay alone. In that regard, the six ITA standards yielded signals of 1,850 RLU (1.3 ng/mL ITA); 3,178 RLU (2.4 ng/mL ITA); 10,940 RLU (8.4 ng/mL ITA); 31,119 RLU (23.1 ng/mL ITA); 123,118 RLU (90.0 ng/mL ITA); and 341,532 RLU (271.8 ng/mL ITA).

These results appear to indicate that the combo assay 820/B152-B207 provides about 2 to 3 times greater sensitivity than the B152-B207 assay alone. Therefore, it will be possible to detect smaller concentrations of ITA in biological samples at earlier time points than possible by currently available assays.

It is also notable that an assay utilizing the purified monoclonal antibody clone 820 alone appeared to result in greater detectable signals than the combo assay 820/B152-B207 or the B152-B207 assay. The results are indicated in FIGS. 1A and 1B designated by the asterisk (*). The 820-B207 assay appears to be approximately 3 to 4 times more sensitive than the B152-B207 assay.

Example 3

ITA/Free Beta hCG Assay

A combination assay ("combo" assay) was also performed using the B152-B207 assay described in Example 1; however, an additional capture antibody to free beta hCG was added to the well during the first incubation with the B152 capture antibody and the ITA. The antibody used was designated clone #827 (purchased from Biodesign International, Saco, Me.; Cat. No. E45575M). This assay is referred to herein as the "combo 827/B152-B207" assay. In particular, in this combo assay, the capture antibodies are the clone 827 and the B152 monoclonal antibodies, and the detection antibody is the B207 monoclonal antibody. The results of this assay are illustrated in FIGS. 1A and 1B designated by the closed square (■).

Even more unexpectedly, the detected signal of ITA appeared to be substantially greater than the detected signal using the B152-B207 assay alone, or the combo 820/B152-B207 assay. In that regard, the six ITA standards yielded signals of 8,033 RLU (1.3 ng/mL ITA); 16,957 RLU (2.5 ng/mL ITA); 55,264 RLU (8.2 ng/mL ITA); 142,512 RLU (22.9 ng/mL ITA); 441,900 RLU (92.2 ng/mL ITA); and 842,974 RLU (267.9 ng/mL ITA).

These results indicate that the combo assay 827/B152-B207 appears to provide about 6 to 12 times greater sensitivity than the B152-B207 assay alone. Therefore, it will be possible to detect smaller concentrations of ITA in biological samples at earlier time points than possible by currently available assays.

It is also notable that an assay utilizing the purified clone 827 alone appeared to result in greater detectable signals than the combo assay 827/B152-B207 or the B152-B207 assay. The results are indicated in FIGS. 1A and 1B designated by the 'x' (x). The 827-B207 assay appears to be approximately 8 to 22 times more sensitive than the B152-B207 assay.

Example 4

A woman five days post ovulation wishes to know if she is pregnant after having sexual intercourse. She leaves a urine sample with her obstetrician. The sample is assayed for ITA using any one of the assays described in Examples 1–3. The amount of ITA measured in the sample is about 1.0 ng/mL. The obstetrician confirms that the woman is pregnant.

Example 5

A woman undergoing fertility treatment is implanted with at least one embryo resulting from in vitro fertilization. Approximately 3 to 4 days after implantation, the woman provides her physician with a urine sample to determine if the implantation was successful. The sample is screened for ITA. The amount of ITA in the sample is about 0.3 ng/mL. The physician confirms that the woman is pregnant.

Example 6

A woman about seven days post ovulation wishes to know if she is pregnant after having sexual intercourse. She obtains a "home pregnancy kit" utilizing any one of the assays described in Examples 1–3. The kit includes a sample cup, a pipette, and an assay device. The assay device comprises a well for the sample, a storage container for the capture antibody solution, a storage container for the detection antibody solution, a storage container for a control solution, an electronic component to control the operation of the assay, and a signal detector, such as a photographic film, or a light bulb. The signal detector detects signals produced by the assay and is preferably set to detect a signal that corresponds to an ITA concentration greater than about 0.18 ng/mL. The sample is pipetted into the sample well of the kit. The assay is performed on the sample. The light bulb for the sample does not emit light, but the light bulb for the control solution does emit light. This confirms that the assay was successful, but that she is not pregnant.

Various publications and/or references have been cited herein, the contents of which are incorporated herein by reference.

While this invention has been described with respect to various specific examples and embodiments, it is to be understood that the invention is not limited thereto and that it can be variously practiced with the scope of the following claims.

We claim:

1. A method for detecting pregnancy in a woman comprising:
   contacting a biological sample of a woman with at least two antibodies that specifically bind different epitopes of ITA, at least one of the two antibodies being coupled to a label effective to produce a chemiluminescent signal; and
   detecting a chemiluminescent signal produced by the label, wherein the presence of a detectable signal indicates pregnancy in the woman.

2. The method of claim 1, wherein the biological sample is a urine sample.

3. The method of claim 1, wherein the label is an acridinium ester.

4. The method of claim 1, wherein the at least two antibodies are monoclonal antibodies designated B152 and B207.

5. The method of claim 4, further comprising contacting the biological sample with an antibody that specifically binds hCG, or a fragment thereof.

6. A method for detecting pregnancy in a woman comprising the steps of:
   a) contacting a biological sample of the woman with a capture antibody designated B152;
   b) contacting the biological sample with a detection antibody designated B207, the detection antibody being coupled to a label that is effective to produce a chemiluminescent signal; and
   c) detecting a signal produced by the label, wherein the presence of a detectable signal indicates pregnancy in the woman.

7. The method of claim 6, wherein the biological sample is obtained within about seven days after ovulation.

8. The method of claim 6, wherein the biological sample is obtained within about five days after ovulation.

9. The method of claim 6, wherein an embryo was implanted into the woman by in vitro fertilization.

10. The method of claim 9, wherein the biological sample is obtained within about four days after in vitro fertilization.

11. The method of claim 6, wherein the biological sample is urine.

12. The method of claim 6, wherein the biological sample is serum.

13. The method of claim 6, farther comprising screening the biological sample for at least one additional pregnancy marker.

14. The method of claim 13, wherein the at least one additional marker is hCG.

15. The method of claim 6, wherein the method is automated.

16. A method for detecting pregnancy in a woman comprising:
    contacting a biological sample of a woman with at least two capture antibodies that specifically bind different epitopes of ITA, and at least one detection antibody that binds an epitope of ITA different from the epitopes bound by the capture antibodies, the detection antibody being coupled to a label that produces a detectable signal in one assay; and
    detection a signal produced by the label, wherein a detectable signal indicates pregnancy in the woman.

17. The method of claim 16, wherein the at least two capture antibodies are designated B152 and clone 827.

18. The method of claim 16, wherein the at least two capture antibodies are designated B152 and clone 820.

19. The method of claim 16, wherein the at least one detection antibody is designated B207.

20. The method of claim 16, wherein the assay is a chemiluminescent assay.

21. The method of claim 16, wherein the biological sample is a urine sample.

22. The method of claim 16, wherein the label is an acridinium ester.

23. The method of claim 16, wherein the biological sample is obtained within about seven days after ovulation.

24. The method of claim 16, wherein the biological sample is obtained within about four days after in vitro fertilization.

25. The method of claim 16, wherein the assay is automated.

26. A method for detecting pregnancy in a woman comprising:
    contacting a biological sample of a the woman with at least two capture antibodies that specifically bind different epitopes of ITA and hCG, and at least one detection antibody that binds an epitope of the ITA and hCG different from the epitopes bound by the capture antibodies, the at least one detection antibody being coupled to a label that is effective to produce a detectable signal in one assay; and
    detecting a signal produced by the label, wherein the presence of a detectable signal indicates pregnancy in the woman.

27. The method of claim 26, wherein the at least two capture antibodies are designated B152 and clone 827.

28. The method of claim 26, wherein the at least two capture antibodies are designated B152 and clone 820.

29. The method of claim 26, wherein the at least one detection antibody is designated B207.

30. The method of claim 26, wherein the assay is a chemiluminescent assay.

31. The method of claim 26, wherein the biological sample is a urine sample.

32. The method of claim 26, wherein the label is an acridinium ester.

33. The method of claim 26, wherein the biological sample is obtained within about seven days after ovulation.

34. The method of claim 26, wherein the biological sample is obtained within about four days after in vitro fertilization.

35. The method of claim 26, wherein the assay is automated.

36. A method for detecting pregnancy in a woman comprising:

contacting a biological sample of a woman with at least two capture antibodies that specifically bind different epitopes of ITA and hCG, one of the capture antibodies being designated B152 and another capture antibody being designated clone 827, and at least one detection antibody, designated B207, that binds an epitope of the ITA and hCG different from the epitopes bound by the capture antibodies, the at least one detection antibody being coupled to a label effective to produce a detectable signal, in one assay; and detecting a signal produced by the label, wherein a presence of a detectable signal indicates pregnancy in the woman.

37. The method of claim 36, wherein the assay is an automated chemiluminescent assay.

* * * * *

UNITED STATES PATENT AND TRADEMARK OFFICE
CERTIFICATE OF CORRECTION

PATENT NO.    : 6,627,457 B2
DATED         : September 30, 2003
INVENTOR(S)   : Pandian et al.

It is certified that error appears in the above-identified patent and that said Letters Patent is hereby corrected as shown below:

<u>Column 14,</u>
Line 34, change "detection" to -- detecting --.
Line 57, after "a" delete the word "the".

Signed and Sealed this

Second Day of March, 2004

JON W. DUDAS
*Acting Director of the United States Patent and Trademark Office*